United States Patent
Parks

(12) 
(10) Patent No.: US 6,399,652 B1
(45) Date of Patent: Jun. 4, 2002

(54) METHOD OF TREATING ACNE VULGARIS USING AVERMECTIN COMPOUND

(76) Inventor: L. Dean Parks, 2420 SE. 15th St., Ocala, FL (US) 34471

( * ) Notice: Subject to any disclaimer, the term of this patent is extended or adjusted under 35 U.S.C. 154(b) by 0 days.

(21) Appl. No.: 09/988,914

(22) Filed: Nov. 19, 2001

Related U.S. Application Data

(63) Continuation-in-part of application No. 09/976,915, filed on Oct. 12, 2001, which is a continuation-in-part of application No. 09/605,747, filed on Jun. 29, 2000, now Pat. No. 6,319,945.

(51) Int. Cl.[7] .............................................. A61K 31/35
(52) U.S. Cl. ...................... 514/453; 514/859
(58) Field of Search ................. 514/453, 859

(56) References Cited

U.S. PATENT DOCUMENTS 5,654,312 A * 8/1997 Andrullis Jt. et al.
5,952,372 A * 9/1999 Mcdaniel
6,136,806 A * 10/2000 Hittel

OTHER PUBLICATIONS

Seavers, A., Cutaneous syndrome possibly caused by heartworm infestation in a dog, Aust. Vet. J. 1998, vol. 76/1, pp. 18–20.*

Osamulia et al., Psoriasis and filariasis, British J. of Derm, 1994. Report from 266th NSDV meeting, pp. 723–724.*

Darge, et al. Ivermectin treatment of hyperactive onchodermatitis . . . , Database Caplus, abstract Trp. Med. Parasitol., 1995, vol. 46/4, pp. 206–212.*

* cited by examiner

Primary Examiner—William R. A. Jarvis
Assistant Examiner—Vickie Kim
(74) Attorney, Agent, or Firm—M. K. Silverman; Yi Li

(57) ABSTRACT

Methods for treating acne vulgaris are disclosed. The treatment includes topical application of a dermatological composition containing an avermectin compound to the affected areas of a patient alone, or in conjunction with other conventional methods of treating acne vulgaris. The dermatological composition contains an avermectin compound in a pharmaceutically acceptable carrier, including water, glycols, alcohols, lotions, creams, gels, emulsions, sprays, soaps, body washes, facial cleansers, and facial masks.

22 Claims, No Drawings

METHOD OF TREATING ACNE VULGARIS USING AVERMECTIN COMPOUND

REFERENCE TO RELATED APPLICATION

This application is a continuation-in-part of patent application Ser. No. 09/976,915 entitled "Method of Treating Dermatoses Using Avermectin Compound" filed on Oct. 12, 2001, which is a continuation-in-part of application Ser. No. 09/605,747 filed on Jun. 29, 2000, patent 6,319,945 both of which are herein incorporated by reference in their entirety.

FIELD OF THE INVENTION

The present invention relates to methods for treating acne vulgaris, particularly with topical treatment using avermectin compound.

BACKGROUND OF THE INVENTION

Acne vulgaris, known as acne by the general public, is a common and multifaceted skin disorder of the hair follicles and sebaceous glands. Although it affects almost 100% of adolescents to varying degrees and generally wanes as adolescence ends, the disease may persist into adulthood. Adult women, in particular, may be affected and may experience premenstrual flares. However, severe acne vulgaris tends to be more common in adolescent males than in people of other age-groups.

At least four factors contribute to the development of acne: follicular plugging, increased sebum production by the sebaceous glands, colonization of the sebaceous follicles with Propionibacterium acnes, and inflammation. Propionibacterium acnes is the most common gram-positive, non-spore forming bacteria, a common resident of the pilosebaceous glands of the human skin. It is the causative agent of acne vulgaris.

Follicular plugging occurs when desquamating cells lining the follicular lumen stick together, rather than flowing to the surface with sebum. This occurs because of abnormal keratinization, components of which are increased cell division and increased cohesiveness of cells lining the follicular lumen. These cells mix with sebum, plug the opening of the hair follicle, and form a closed comedo (commonly called whitehead). If this mixture protrudes from the follicular opening, it turns a dark color (blackheads).

During adolescence, when sebum production increases, the sebaceous follicles become colonized with Propionibacterium acnes. This anaerobic diphtheroid hydrolyzes sebum into free fatty acids, which serve as the primary proinflammatory substances of acne vulgaris. Propionibacterium acnes also secrete chemotactic factors that attract neutrophils. Lysosomal enzyme released from the neutrophils rupture the follicle wall releasing proinflammatory mediators including keratin and lipids into the surrounding dermis. The resulting inflammation forms erythematous papules or pustules, nodules, cysts, or abscesses. If the inflammation is severe, as in cystic acne, the skin may eventually scar.

Therefore, the key features of the pathogenesis of acne vulgaris can be characterized as 1) increased sebum production, 2) hyperkeratinization of the neck of the follicles, 3) bacterial proliferation, and 4) inflammation.

Acne vulgaris can be classified into three categories: comedonal, inflammatory, and nodulocystic. Within each category, acne vulgaris can be further divided into mild, moderate, or severe, based on the number of lesions and the amount of skin involved.

Comedonal acne consists predominantly of open or dosed comedones with generally few, if any, inflammatory lesions. Comedonal acne generally responds to existing topical keratolytic agents, which decrease the adhesiveness of follicular cells. Inflammatory acne consists of comedonal lesions plus inflammatory lesions, such as erythematous papules and pustules. It generally requires treatment with both topical agents and systemic antibiotics. By comparison, nodulocystic acne comprises extensive comedonal lesions and inflammatory papules and pustules, plus nodules and cysts or abscesses. Existing topical agents are not effective for initial treatment of these lesions.

Effective management of acne vulgaris can be accomplished by addressing the four key features of the pathogenesis. Topical therapy is usually the first choice for patients with mild-to-moderate inflammatory acne. The use of topical therapy minimizes potential side effects associated with the use of systemic agents. Topical therapies include benzoyl peroxide, which is the most commonly used non-prescription acne medication. It is an important antibacterial oxidizing agent that can decrease the number of Propionibacterium acnes and frequently the amount of free fatty acids. Benzoyl peroxide is the first line monotherapy for mild acne vulgaris and it is available in over-the-counter preparations. Benzoyl peroxide is applied once or twice daily and patients often experience mild redness and scaling of the skin during the first week of usage.

Tretinoin is the most effective topical comedolytic agent currently, decreasing the cohesiveness of follicular epithelial cells, and thereby inhibiting the formation of microcomedones and increasing cell turnover resulting in expulsion of existing comedones. This agent also decreases the thickness of the stratum corneum and potentiates the penetration of topical antibiotic agents. Tretinoin therapy comprises once daily application. Mild redness and peeling are a part of the therapeutic effect of the medication but can result in reduced patient compliance. The improvement may take as long as 6 to 12 weeks, and flare-ups of acne vulgaris can occur during the first few weeks of therapy.

Mild inflammatory acne vulgaris lesions can also be treated with topical antibiotics including erythromycin ointment, clindamycin solution, and meclocylcine cream. The primary action of the antibiotics is to reduce the population of Propionibacterium acnes in the sebaceous follicle and thereby suppress the free fatty acid production. The effectiveness of topical antibiotics in the treatment of acne is limited by their low lipid solubility and subsequent difficulty in penetrating sebum-filled follicles. Topical antibiotics are applied twice daily.

Patients with moderate to severe inflammatory acne often require oral antibiotics in addition to topical therapy. The most commonly prescribed agents include tetracycline, erythromycin, minocycline, and doxycycline. Treatment is usually maintained for several months. Side effects include the overgrowth of nonsusceptible organisms, including Candida, which can produce vaginal and oral yeast infections.

Patients with severe inflammatory acne vulgaris unresponsive to other therapy may require treatment with oral isotretinoin. Isotretinoin is a compound related to vitamin A, and is the only agent that decreases sebum production and reverses the abnormal epithelial formation process. This agent can also decrease number of Propionibacternum acnes in the sebaceous follicle. Duration of therapy is usually 20 weeks, and the satisfactory response rate is quite high. However, treatment is often accompanied by many side effects, including dry skin, pruritus, epistaxis, and photosensitivity, as well as hypertriglyceridemia, abnormal liver function tests, electrolyte imbalances, and elevated platelet counts. Most serious though, is the teratogeric effect of isotretinoin. Use of isotretinoin during pregnancy is absolutely contraindicated. So serious is the potential for death or teratogenic effects to a fetus, isotretinoin is practically contraindicated in women of child-bearing age. Use of isotretinoin must be accompanied by a guarantee by the patient that conception will be avoided at any and all costs.

Because acne vulgaris is a multifactorial disease which is manifest to varying degrees, it is important for the physician to assess the patient to attempt to find therapies which will be helpful to the patient without causing major side effects. All of the current conventional treatments are associated with some degree of adverse side effects that limit their usefulness. Consequently, there is a need for a drug that can effectively treat acne vulgaris without side effects.

The preferred compound that is used to illustrate the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. The following molecular structure represents the avermectin series of compounds, which can be chemically converted to useful derivatives as discussed below.

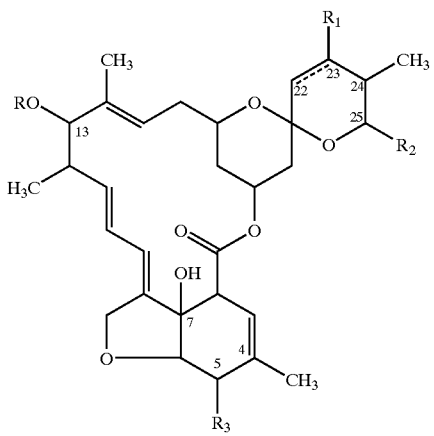

wherein R is the 4'-(alpha-L-oleandrosyl)-alpha-L-oleandrose group of the structure:

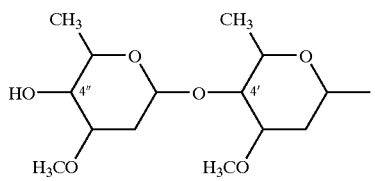

wherein the broken line indicates a single or double bond; $R_1$ is hydroxy and is present only when said broken line indicates a double bond; $R_2$ is isopropyl or secbutyl; and $R_3$ is methoxy or hydroxy.

The avermectins (of which ivermectin, a chemically produced analog, is a member) are a series of compounds isolated from the fermentation broth of a C-076 producing strain of *Streptomyces avermitillis* and also chemically produced derivatives thereof. There are eight different but closely related compounds produced by *S. avermitillis*, designated as $A_{1a}$, $A_{1b}$, $A_{2a}$, $A_{2b}$, $B_{1a}$, $B_{1b}$, $B_{2a}$, and $B_{2b}$. The production of these compounds is described in U.S. Pat. No. 4,310,519. The preparation of ivermectin is disclosed in U.S. Pat. No. 4,199,569. The disclosures of each of the foregoing patents are incorporated herein by reference. The avermectin family of compounds is a series of very potent antiparasitic agents known to be useful against a broad spectrum of endoparasites and ectoparasites in mammals and also to have agricultural uses against various nematode and insect parasites found in and on crops and in soil.

Some of the avermectins contain a 22,23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571; the latter patent also describes the 13-halo derivatives. The avermectin compounds and derivatives have several hydroxy groups which may be acylated as described in U.S. Pat. No. 4,201,861. U.S. Pat. No. 5,055,454 describes inverting position 13 of avermectin from a normal alpha stereochemistry to the epimeric 13-beta stereochemistry. U.S. Pat. No. 5,077,308 describes avermectin aglycone derivatives which incorporate a ketal at position 13. U.S. Pat. No. 5,162,363 describes avermectin derivatives where the 23-position ring carbon atom is replaced with by sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All the aforementioned patents are incorporated herein by reference. The compounds disclosed in the patents mentioned above share the property of antiparasitic activity with ivermectin.

All avermectin compounds mentioned and referred to above share the spectrum of anti-parasitic biological activity of ivermectin, varying only in degree. It is expected that they will share the activity spectrum of ivermectin needed for them being suitable to use for the purpose of the present invention.

Ivermectin has been used as an antiparasitic agent to treat various animal parasites and parasitic diseases since mid-1980's. It is commercially available for animal use as Cardomec® (for felines), Eqvalane® (for equines) and Ivomec® (for bovines) by Merial, a Merck and Aventis company; as Zimecterin® (for equines) by Famam Companies, Inc., Omaha, Nebr. The medicine is available in tablets and chewables for heartworm prevention, topical solution for ear mite treatment, and injectable solution, or oral paste or solution for other parasite problems.

Ivermectin is also commercially available from Merck & Co., Inc for human use as Stromectol® for eradication of threadworm *Strongyloides stercoralis*, and for eradication of *Onchocerca volvulus*. Stromectol® was approved by the U.S. Food and Drug Administration to treat nondisseminated intestinal threadworm (strongyloidiasis) in March 1997. Stromectol® has also been cleared by the U.S. Food and Drug Administration to treat onchocerciasis, or river blindness. The medicine is available in tablets and is orally administered by the patients. The recommended dose of Stromectol® for the treatment of intestinal strongyloidiasis is a single oral dose, two 6 mg tablets for average weight adults (200 micrograms per kilogram of body weight).

Stromectol® can also be used in children who weigh 15 kg (33 lb.) or more, at a dose ranging from ½ to 2 tablets.

Magda et al. Amer. J. Trop. Med. Hyg. 53(6) 1995 pp. 652–653 describe a method of topical application of ivermectin to treat head lice. Ivermectin is found to have an absolute curative effect after a single topical application.

U.S. Pat. No. 5,952,372 (to McDaniel) discloses a method of treating a form of rosacea associated with the ectoparasite Demodex by orally administering or topically applying ivermectin to fill and eliminate *Demodex Follicuorum* mites from hair follicles in affected skin. Such treatment results in cessation of the manifestations of allergic and vasomotor responses to the organism that cause the symptoms and signs of rosacea.

U.S. Pat. No. 6,133,310 (to Parks) discloses a method of treating acne rosacea by topically applying ivermectin to the affected areas. Acne rosacea is a different dermatological disease, in term of etiology and histology, from acne vulgaris which is addressed in the present invention. Differential diagnosis is important for the patients to obtain an appropriate treatment and effective prevention of their conditions.

SUMMARY OF THE INVENTION

Accordingly, it is an object of the invention to provide an effective topical treatment of acne vulgaris.

In one embodiment, the present invention relates to a method of treating acne vulgaris comprising topically applying a therapeutically effective amount of an avermectin compound to an affected area of a patient.

The avermectin compound is in a dermatological composition comprising an effective amount of the avermectin compound and a pharmaceutically acceptable carrier including water, glycols, alcohols, lotions, creams, gels, emulsions, sprays, soaps, body washes, facial cleansers, and facial masks. The dermatological composition can also be integrated into medicated tape, topical dressing, dermal patch, or cleansing tissue. The avermectin compound includes avermectins, avermectin derivatives, preferably ivermectin and ivermectin derivatives. The concentration of the avermectin compound in the dermatological composition is from about 0.05% to about 8% (w/v, or w/w). In a preferred embodiment, ivermectin is used.

In a further embodiment, the present invention relates to a method of treating acne vulgaris comprising the steps of: (a) topically applying an initial dosage of an avermectin compound to an affected area of a patient for an initial treatment period, and (b) thereafter topically applying a maintenance dosage of an avermectin compound to the affected area for maintenance.

In an additional embodiment, the present invention further relates to a dermatological kit for treating acne vulgaris. The kit includes a dermatological composition comprising avermectin compound and a pharmaceutically acceptable carrier in a container, and written instructions on or associated with the container, on how to use the dermatological composition for treating acne vulgaris.

DETAILED DESCRIPTION OF THE INVENTION

The present invention relates to a method of treating acne vulgaris. In one embodiment, the method comprises topical application of a therapeutically effective amount of an avermectin compound to affected areas of a patient.

The avermectin compounds for the purpose of the present invention include avermectin, avermectin derivatives, ivermectin, and ivermectin derivatives. The avermectin compound is preferably mixed with a pharmaceutically acceptable carrier or a base which is suitable for topical application to skin, to form a dermatological composition. Suitable examples of carrier or base include, but not limited to, water, glycols, alcohols, lotions, creams, gels, emulsions, and sprays. Furthermore, the dermatological composition containing an avermectin compound can be integrated into a topical dressing, medicated tape, dermal patch and cleansing tissues. Additionally, the avermectin compound can be added into soap, body wash, facial cleanser, and facial mask. Examples 1 to 3 provide various topical dermatological compositions containing an avermectin compound for treatment acne vulgaris.

In a preferred embodiment, ivermectin is used because it is readily available commercially. The concentration of ivermectin in the dermatological composition for the purpose of the present invention can be in a broad range from about 0.05% to 8% weight by volume (w/v), or weight by weight (w/w) depending on the form of the carrier. When the carrier is water, measuring by volume is convenient. However, when the carrier is gel or cream, measuring by weight is more convenient. It has been found that a lotion or a cream containing ivermectin at a concentration as low as 0.075% is clinically effective in treating acne vulgaris.

Preferably, in an initial treatment of acne vulgaris the ivermectin dermatological composition can be applied topically from one to several times daily for a period of from about one week to several weeks (for example, two to six weeks), to substantially control the condition and clear the lesions. The initial dosage, including frequency of the topical application, ivermectin concentration of the dermatological composition, and the length of the initial treatment period can be determined depending on a specific type of acne vulgaris, severity of the disease, and the response of the patient to the medication. After the initial treatment, a maintenance dosage, that has less frequent application, and/or a dermatological composition with less concentration of ivermectin, can be used for maintaining the condition.

It has been found in an informal clinical trial using the method of the present invention that topical application of ivermectin to skin affected by acne vulgaris has the following advantageous properties: (1) it removes skin irritation caused by acne vulgaris; (2) it clears up lesions; (3) it is anti-inflammatory and controls inflammation of the affected area; (4) it has antimicrobial property and controls dermal infection of the affected area; and (5) it is safe and has no side effects observed in any body locations.

The choice of the ivermectin concentration, and the form of the dermatological composition for treatment of acne vulgaris can be made depending on the type of acne vulgaris and severity of the diseases, location of the affected area, and form of the dermatological composition.

To treat most patients diagnosed with acne vulgaris, a lotion containing about 0.05% to 0.2% of ivermectin can be used. In the case of treating acute conditions, a more potent composition containing higher concentration of ivermectin can be used. On the other hand, for prolonged maintenance of certain conditions, a low concentration such as from about 0.05% to about 0.1% is preferred.

Acne vulgaris can occur near the eyes, such as on the eye brows. To treat skin near eyes, a high concentration of the medicine should be avoided to prevent irritation of the eyes. It is found that a 0.075% ivermectin lotion does not cause eye irritation when it is used on the face, or near the eyes.

In the form of body wash, soap, facial cleanser, and facial mask the concentration of ivermectin is higher, such as about 2% to about 8%, because the medicine is not retained on the skin after rinsing, and treatment time is short. On the contrary, in the forms of topic dressing, medicated tape, and dermal patch the medicine stays on the treated area longer than other forms, therefore, the concentration of ivermectin can be lower.

Optionally, a combination of different forms of topical treatment can also be used. For example, an ivermectin tape can be used in the night, and an ivermectin cream or lotion can be used during the day. The ivermectin body wash, soap, facial cleanser, and facial mask can be used in combination with any of other topical applications.

The dermatological composition containing ivermectin can be sold as a kit wherein the composition is packaged in a container, such as a plastic container. Written instructions on how to use the dermatological composition in accordance with the present invention are included on or associated with the container, which provides instructions for treating acne vulgaris.

Although the inventor is not bound by any theoretical explanation as to why the composition and the method of the present invention are effective in treating acne vulgaris, presentation of certain theoretical understanding may be of value. Based on the clinical observations, it is believed that one reason for the efficacy of the composition and the method of the present invention is due in part to anti-microbial property of ivermectin.

Another possible reason for the efficacy of the composition and the method of the present invention is that the ivermectin dermatological composition has anti-inflammatory effect. It is believed that ivermectin exerts an anti-inflammatory effect on the cells of the sebaceous gland unit, thus decreasing production of neutrophils and lymphocytes which contribute to inflammation.

Ivermectin has been used as an oral medication for treatment of river blindness in human caused by *Onchocerca volvulus* parasite since late 1980s. With an oral dosage of a moderate ivermectin concentration, this medicine is safe in human, without serious adverse side effects. Therefore, topical treatment of acne vulgaris using ivermectin dermatological composition and the method of the present invention is safe to human patients, which was demonstrated by the clinical examples described hereinafter. Furthermore, as discussed previously that a dermatological composition having ivermectin concentration as low as 0.075% is clinically effective in treating acne vulgaris. Such a low concentration is advantageous because it reduces risks of adverse side effects, and reduces the possibility of triggering body's autoimmune responses.

In a further embodiment, the present invention relates to a method of treating acne vulgaris which comprises (a) topically applying to the affected areas of the patient a therapeutically effective amount of avermectin compound; (b) administering to a patient a therapeutically effective amount of at least one other conventional anti-acne medication, which includes, but not limited to, benzoyl peroxide, sulfur, resorcinol, salicydic acid, opioid, tretinoin, antibiotics, and isotretinoin. The conventional medications should be used in conventional doses. In this case, the avermectin compound is used in conjunction with conventional acne treatment as an adjuvant. The combinational treatment is beneficial for treating a multifactorial disease like acne vulgaris.

Operating with the informed consent of the patients who had suffered from acne vulgaris, and their conditions had failed to improve by using existing treatment methods or were not appropriate to use existing medications, the patients were treated with the ivermectin dermatological composition and the method of the present invention. Examples 4 and 5 illustrate clinical effectiveness of the method of the present invention.

EXAMPLE 1

A topical dermatological composition containing avermectin compound is obtained as follows.

Mix 0.15 g of ivermectin, manufactured by Merck & Co., Inc., sufficiently with 100 ml of deionized water to make an aqueous suspension, wherein the concentration of ivermectin is 0.15% (w/v). Sodium hydroxide and citric acid can be used to adjusted pH of the suspension to about 7.

Other suitable composition can be made in accordance with Example 1 which include ivermectin in the following concentrations: 0.05%, 0.075%, 0.2%, 0.5%, and 1% (w/v).

EXAMPLE 2

A topical dermatological lotion containing avermectin compound is obtained as follows.

Mix 0.075 g of ivermectin, manufactured by Merck & Co., Inc., sufficiently with 100 ml of Cetaphil® moisturizing lotion, manufactured by Galderma Laboratories, Inc., Fort Worth, Tex., to make an ivermectin lotion, wherein the concentration of ivermectin is 0.075% (w/v).

Other suitable compositions can be made in accordance with Example 2 which include ivermectin in the following concentrations: 0.05%, 0.1%, 0.2%, 0.5%, 1%, 4%, and 8% (w/v or w/w) in the base of Cetaphil® moisturizing lotion. Other compatible commercial available lotions can also be used as a base or carrier.

The Cetaphil® moisturizing lotion is a carrier of the ivermectin, which contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, famesol, benzyl alcohol, phenoxyethanol, acrylates/C10-30 alkyl acrylate crosspolymer, sodium hydroxide, citric acid.

EXAMPLE 3

A medicated body wash containing an avermectin compound is obtained as follows.

Mix 5 g of ivermectin, manufactured by Merck & Co., Inc., sufficiently with 100 ml of a body wash liquid to make an ivermectin body wash, wherein the concentration of ivermectin is 5% (w/v).

Other suitable compositions can be made in accordance with Example 3 which include ivermectin in the following concentrations of 1%, 3%, and 8% (w/v or w/w) in a base of body wash. The body wash base can be a solution, a gel, or an emulsion.

EXAMPLE 4

A 20 year old pregnant woman developed pustulocystic acne, one type of acne vulgaris, during the latter months of pregnancy. Therapy was limited to topical treatment including benzoyl peroxide, Retin-A (tretinoin), and hydrocortisone lotion. In spite of these treatments, her condition continued to worsen even after delivery. The patient had two large cysts on the right cheek which her physician had scheduled for surgery. Oral antibiotics were not a choice of treatment because she was nursing.

The patient was treated with topical application of the 0.075% ivermectin lotion of Example 2 daily at bed time. In three weeks, her condition improved substantially, and the "cyst surgery" was cancelled because it was no longer needed. A maintenance dosage of topical application of the lotion twice a week was instituted thereafter for four weeks, and the patient had a total clearing.

EXAMPLE 5

A 12 year old girl had extensive comedo-pustular acne (another type of acne vulgaris) on the brow, nose and malar areas. She was treated with Retin-A and benzoyl peroxide. The patient was very distraught because of the redness, inflammation and pustulation. For this reason she was treated with topical application of the 0.075% ivermectin lotion of Example 2 once to twice daily, in addition to her existing conventional treatments. Within two weeks, all of the redness and pustules were gone. Retin-A therapy was continued to the residual comedones.

In the informal trials, no adverse side effects or contraindications were observed among the patients. The patients had no complaints of skin irritation during the initial treatment, or prolonged maintenance treatment. There was no report of increasing skin sensitivity.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of treating acne vulgaris comprising topically applying a therapeutically effective amount of an avermectin compound to an affected area of a human patient.

2. The method of claim 1, wherein said avermectin compound is in a dermatological composition comprising an effective amount of said avermectin compound and a pharmaceutically acceptable carrier.

3. The method of claim 2, wherein said pharmaceutically acceptable carrier comprises water, glycols, alcohols, lotions, creams, gels, emulsions, sprays, soaps, body washes, facial cleansers, and facial masks.

4. The method of claim 3, wherein said dermatological composition is integrated in medicated tape, topical dressing, dermal patch, or cleansing tissue.

5. The method of claim 4, wherein said avermectin compound comprises avermectins, avermectin derivatives, ivermectin, or ivermectin derivatives.

6. The method of claim 5, wherein said avermectin compound in said dermatological composition is in a concentration greater than about 0.05%.

7. The method of claim 5, wherein said avermectin compound in said dermatological composition is in a concentration range from about 0.05% to about 8%.

8. A method of treating acne vulgaris comprising the steps of:
(a) topically applying an initial dosage of a therapeutically effective amount of an avermectin compound to an affected area of a human patient for an initial treatment period, and
(b) thereafter topically applying a maintenance dosage of an avermectin compound to said affected areas for maintenance.

9. The method of claim 8, wherein said initial treatment period is from about one week to several weeks.

10. The method of claim 8, wherein said avermectin compound comprises avermectins, avermectin derivatives, ivermectin, or ivermectin derivatives.

11. A method of treating acne vulgaris comprising topically applying a therapeutically effective amount of ivermectin to an affected area of a human patient.

12. The method of claim 11, wherein said ivermectin is in a dermatological composition comprising an effective amount of said ivermectin and a pharmaceutically acceptable carrier.

13. The method of claim 12, wherein said pharmaceutically acceptable carrier comprises water, glycols, alcohols, lotions, creams, gels, emulsions, sprays, soaps, body washes, facial cleansers, and facial masks.

14. The method of claim 13, wherein said dermatological composition is integrated in medicated tape, topical dressing, dermal patch, or cleansing tissue.

15. The method of claim 12, wherein said ivermectin in said dermatological composition is in a concentration greater than about 0.05%.

16. The method of claim 12, wherein said ivermectin in said dermatological composition is in a concentration range from about 0.05% to about 8%.

17. A method of treating acne vulgaris comprising the steps of:
(a) topically applying an initial dosage of a therapeutically effective amount of ivermectin to an affected area of a human patient for an initial treatment period, and
(b) thereafter topically applying a maintenance dosage of ivermectin to said affected area for maintenance.

18. The method of claim 17, wherein said initial treatment period is from about one week to several weeks.

19. A method of treating acne vulgaris comprising:
(a) topically applying to the affected areas of a human patient a therapeutically effective amount of avermectin compound, and
(b) administering to said patient a therapeutically effective amount of at least one other anti-acne medication.

20. The method of claim 19, wherein said at least one other anti-acne medication comprises benzoyl peroxide, sulfur, resorcinol, salicydic acid, opioid, tretinoin, antibiotics, and isotretinoin.

21. The method of claim 19, wherein said avermectin compound comprises avermectins, avermectin derivatives, ivermectin, or ivermectin derivatives.

22. The method of claim 21, wherein said avermectin compound is in a dermatological composition comprising said avermectin compound in a concentration greater than about 0.05%, and a pharmaceutically acceptable carrier.

* * * * *